US008763177B2

(12) United States Patent
Shah et al.

(10) Patent No.: US 8,763,177 B2
(45) Date of Patent: Jul. 1, 2014

(54) POSITIONING DEVICE AND METHOD OF USE

(75) Inventors: Bharat Shah, Springfield, MO (US); Dawn Zablocki, Springfield, MO (US); Sami Khoshyomn, Springfield, MO (US)

(73) Assignee: Mercy Medical Research Institute, Springfield, MI (US)

( * ) Notice: Subject to any disclaimer, the term of this patent is extended or adjusted under 35 U.S.C. 154(b) by 0 days.

(21) Appl. No.: 13/592,299

(22) Filed: Aug. 22, 2012

(65) Prior Publication Data

US 2013/0074264 A1 Mar. 28, 2013

Related U.S. Application Data

(60) Provisional application No. 61/526,074, filed on Aug. 22, 2011.

(51) Int. Cl.

| | |
|---|---|
| ***A47B 13/00*** | (2006.01) |
| ***A47C 20/00*** | (2006.01) |
| ***B68G 5/00*** | (2006.01) |
| ***A61F 5/37*** | (2006.01) |
| ***A61B 19/00*** | (2006.01) |

(52) U.S. Cl.
USPC ............ 5/603; 5/655; 5/657; 5/632; 128/846; 128/869; 128/870

(58) Field of Classification Search
USPC ..................... 5/603, 640, 655, 657, 632, 637; 128/845, 846, 869, 870, 875
See application file for complete search history.

(56) References Cited

U.S. PATENT DOCUMENTS

| | | | | |
|---|---|---|---|---|
| 3,215,834 | A * | 11/1965 | Tayman | 378/174 |
| 3,306,287 | A * | 2/1967 | Arp | 128/847 |
| 3,967,128 | A * | 6/1976 | Smulewicz | 378/174 |
| 4,819,287 | A * | 4/1989 | Halverson | 5/710 |
| 4,840,362 | A * | 6/1989 | Bremer et al. | 5/632 |
| 4,937,901 | A | 7/1990 | Brennan | |
| 5,048,136 | A * | 9/1991 | Popitz | 5/603 |
| 5,357,982 | A * | 10/1994 | Shaw | 5/621 |
| 5,387,177 | A * | 2/1995 | Dunn | 600/22 |
| 5,524,640 | A * | 6/1996 | Lisak et al. | 5/655 |
| 5,588,445 | A * | 12/1996 | Obaidi | 128/846 |
| 5,606,744 | A * | 3/1997 | Lindy | 2/467 |
| 5,613,501 | A * | 3/1997 | Michelson | 5/637 |
| 5,860,176 | A | 1/1999 | Norberg | |
| 6,966,087 | B2 | 11/2005 | Robinette | |
| 7,496,980 | B2 * | 3/2009 | Sharps | 5/621 |
| 7,712,169 | B2 * | 5/2010 | Kovalyak | 5/655 |
| 7,716,764 | B2 * | 5/2010 | Joe et al. | 5/655 |
| 8,146,599 | B2 * | 4/2012 | Wilson et al. | 128/845 |
| 8,393,329 | B2 * | 3/2013 | Snow et al. | 128/845 |
| 2008/0092300 | A1 | 4/2008 | Joe et al. | |
| 2009/0031500 | A1 | 2/2009 | Daly et al. | |
| 2010/0122414 | A1 * | 5/2010 | Shah | 5/603 |
| 2011/0162657 | A1 * | 7/2011 | Tullous | 128/845 |
| 2011/0219546 | A1 * | 9/2011 | West | 5/621 |
| 2012/0247483 | A1 * | 10/2012 | Flynn | 128/845 |
| 2012/0284925 | A1 * | 11/2012 | Bennett | 5/655 |

* cited by examiner

*Primary Examiner* — William Kelleher
*Assistant Examiner* — Eric Kurilla
(74) *Attorney, Agent, or Firm* — Lathrop & Gage LLP

(57) ABSTRACT

A positioning device is described for supporting an infant with myelomeningocele during surgery, transport and pre- and post-operative procedures. The device allows the patient to be expeditiously re-positioned from prone to supine and lateral positions and vice versa before, during and after surgery. The device allows access to the myelomeningocele while the patient is secured in the device.

3 Claims, 9 Drawing Sheets

POSITIONING DEVICE AND METHOD OF USE

CROSS REFERENCE TO RELATED APPLICATIONS

This non-provisional application claims priority of U.S. Provisional Patent Application No. 61/526,074 filed on Aug. 22, 2011, which is incorporated herein by reference.

BACKGROUND

1. Field of the Invention

The positioning device is in the field of devices for positioning patients during surgery, and during pre- and post-operative procedures. More specifically, the positioning device relates to devices for positioning patients with myelomeningocele, commonly known as a type of spina bifida, during surgery. The positioning device is in the field of positioning devices for infants.

2. Description of the Related Art

Various devices and supports have been developed to allow medical personnel to reposition a patient during surgery with a minimum of dislocation and relative movement of the patient's body. One such device is described in U.S. Pat. No. 4,937,901 for Apparatus for Turning a Patient from a Supine to a Prone Position and Vice Versa which discloses an apparatus for use during surgery to rotate a patient from a supine to a prone position or in the opposite manner. The apparatus comprises a frame to which the patient is secured by straps or fabric. The frame has supports that maintain it at a certain height above the floor and that may be extended to lift the patient above an operating table.

The section of the frame to which the patient is attached is rotatably attached to the other portions of the frame, allowing that part of the frame, and the patient secured to it, to be rotated from a prone position to a supine position and back. The frame is a heavy, bulky apparatus that is not well-suited to transporting the patient or to long-term attachment to a patient. The apparatus also maintains the patient in a flat position with arms, legs and hips fully extended.

Similarly, a device for supporting a patient with spina bifida is described in Patent Application Publication US 2008/0092300 A1 for Infant Positioner which discloses a device for supporting an infant in the fetal position and prone. The base of the device is shaped to hold the limbs of the infant in a desired fetal configuration, and straps are provided to hold the infant on the base. The base allows the infant to rest in the fetal position but only in a prone position for access to the infant's back. The base is specifically designed for use with infants with spina bifida. No support to allow supine or lateral positioning is described, only prone positioning.

SUMMARY OF THE INVENTION

The positioning device described herein provides a device that is capable of holding a patient with spina bifida in either a prone or supine position, and in some embodiments, a lateral position. The device is portable, allowing the patient to be transported to and from surgery secured in the device. A method of utilizing the device is also described herein and with reference to the figures.

A positioning device for positioning a patient in either a prone or supine position comprises a frontal, or anterior, support, a posterior support, and straps for releasably connecting the frontal support to the posterior support. In embodiments, the frontal support comprises a base, a headpiece and at least one vertical support, and the posterior support comprises a base, a neck support and a dorsal opening.

A method of supporting a patient in a prone or supine position comprises the steps of providing a frontal support comprising a base, a headpiece and at least one vertical support; providing a posterior support comprising a base, a neck support and a dorsal opening; placing the patient in a supine position on the posterior support, placing the frontal support on the patient, and securing the frontal support to the posterior support.

DETAILED DESCRIPTION

The positioning device provides an improved device for supporting a patient in prone, supine and lateral positions during surgical procedures and during transport to and from such surgical procedures. The positioning device, in the embodiment shown in the figures, is useful in the treatment of patients with myelomeningocele, often referred to as spina bifida. Such patients have various degrees of exposed spinal tissue in the lumbar or sacral areas of the back, including the nerve tissue in the spinal cord and meningeal membrane.

The exposed spinal elements make it impractical to position the patient in a supine position due to the risk of damage to or infection of the exposed spinal tissue. If the patient is supported in the supine position it is difficult and time-consuming to provide supports to hold the patient in the desired position, without contact to the exposed spinal elements. Such support may be compromised by movement of the patient or movement during transport or manipulation of the patient by surgical staff. Further, it is often desirable to position the patient in both prone and supine positions during the course of surgery and transport to and from surgery, and to interchange the patient between positions without excessive delay and increased risk of trauma to the exposed spinal tissue.

The positioning device provides a device to support a patient allowing quick re-positioning of the patient between the supine, prone or lateral positions during surgery or transport. The patient is positioned between two supports, described in more detail with respect to the figures below, which are formed to contour to the patient's body, both frontal (or anterior) and posterior surfaces. The supports are releasably attached to each other fixing the patient between the supports. The outer surfaces of the supports are capable of disposition on any level surface to hold the patient in the desired position, prone, supine or lateral.

Figure 1:
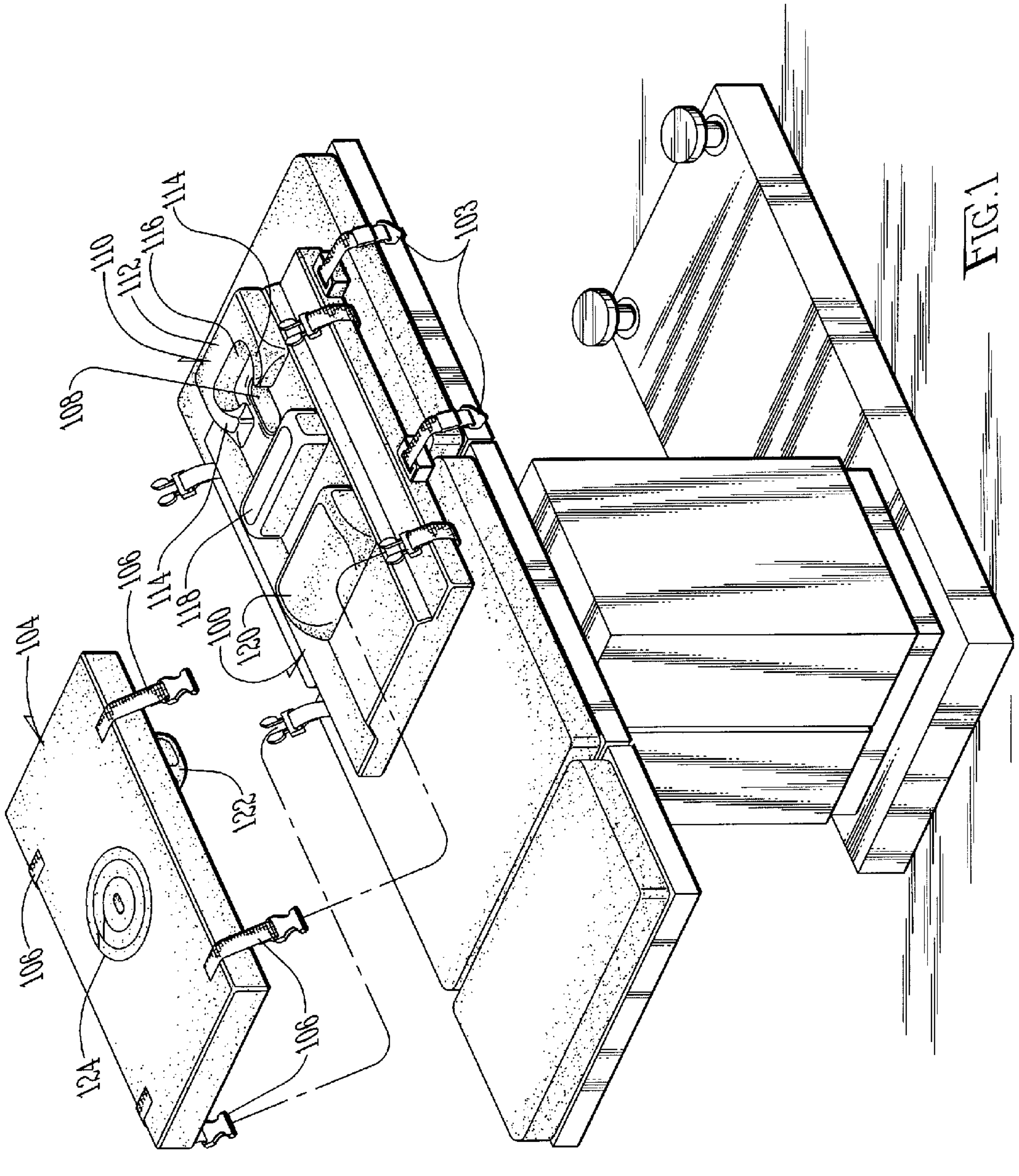
FIG. 1 is a perspective view of an embodiment of the positioning device.

Referring now to FIG. 1, a perspective view of an embodiment of the dual positioning device is depicted, partially installed on a surgical table. The device generally comprises a frontal, or anterior, support 100 which is positioned adjacent to the front of the patient 102, and a posterior support 104 positioned adjacent to the posterior of the patent 102. Straps 103 may be optionally provided to secure the frontal support 100 to the surgical table.

The supports 100 and 104 are formed from a material that is supportive but provides flexibility and compressibility to contour to the patient's body while continuing to provide structural support. Such materials include, but are not limited to, appropriate types of open or closed cell foam, and other materials exhibiting the described characteristics may be utilized within the scope of this disclosure. The material may be encased in a covering to provide, among other benefits, (i) protection from stains, (ii) ease of cleaning or sterilization or (iii) improved skin contact characteristics. The supports may also be formed from appropriate disposable materials for single use only.

The frontal support 100 and the posterior support 104 are positioned adjacent to the patient 102 and secured to each other by means of a plurality of straps 106. The straps 106 may be disconnected from one or both of the supports 100 and 104 to ease the placing or removing of the patient 102 on or from the positioning device, and also provide a means for pulling the supports 100 and 104 closer together and tightening their fit against the patient 102. The support 100 comprises a base 101 and various supports extending thereform and described in more detail in relation to later figures. The base 101 may have a raised central area, and the base 101 and the supports described below may be assembled from various components or they may be formed from a unitary piece of material, whether by casting, milling, molding or otherwise.

The straps 106 may be formed of commonly used materials for straps, including synthetic or natural fiber materials formed into a woven strap, or plastic materials formed into a solid, extruded or cast strap. Any other type of strap with appropriate properties may be utilized for the straps 106. In the embodiment shown in the Figures, the straps 106 are releasably attached to supports 100 and 104 by hook and loop closure, snaps, or other types of releasable attachments, or may be held in place by friction once tightened around the supports and a patient. In other embodiments the straps 106 may be sewed or permanently attached to supports 100 and 104, and provided with adjustable buckles or quick release closures to provide releasable and adjustable connection between the frontal and posterior supports 100 and 104.

In FIG. 1, the positioning device is shown disposed on a surgical table in the prone orientation for securing the patient in the prone position. The frontal support 100 is provided with a facial support area having one or more facial apertures 108 to allow health care personnel to access the face of the patient 102 while the patient is secured in the positioning device. The aperture 108 also allows tubes, hoses, wires or other connections for life support or diagnostic equipment to be utilized while the patient 102 is secured in the positioning device. The aperture may be a variety of shapes and sizes depending on the needs of the users of the positioning device, but typically provides unobstructed access to the mouth and nasal areas of the patient 102. The positioning device may be secured to the surgical table, or it may be simply placed on the surgical table during surgery.

The frontal support 100 is also provided with supports designed to support the various areas of the patient's body without interfering with breathing and access by medical personnel to the patient. In the embodiment shown in FIG. 1, various support pads are provided to support the body of the patient 102 in the desired position. In the embodiment shown in FIG. 1, a facial support 110 is provided for supporting the head of the patient 102. The facial support 110 may be of various sizes and shapes, but is typically provided with a forehead support area 112 and cheek support areas 114. The facial support 110 typically is provided with an aperture 116 around the areas of the eye so that the facial support 110 does not impinge on the eyes of the patient 102.

In the embodiment shown in FIG. 1, the frontal support 100 is also provided with a chest support 118 and a pelvic support 120. The pelvic support 120 is typically sloped or curved toward the legs of the patient 102 to provide comfortable and ergonomic support to the upper thigh area of the legs. Other embodiments of the positioning device may incorporate different configurations of supports without varying from the scope and intent of the disclosed invention.

The posterior support 104 is optionally provided with a variety of supports for engaging the posterior surface of the body of patient 102. The posterior support 104 shown in FIG. 1 is provided with a single neck support 122 for engaging and supporting the back of the neck of the patient 102. In some embodiments, the neck support 122 may be removable and may be moved to the appropriate location for the patient and reattached to the support 104. Neck support 122 may also be removed entirely during use. The posterior support 104 is also provided with an adjustable dorsal opening 124 for providing access to the dorsal area of the patient.

The support pads 110, 118, and 120 described with reference to FIG. 1 may be formed separately from the supports 100 and 104 or may be formed with supports 100 and 104 from a unitary piece of material.

Figure 2:
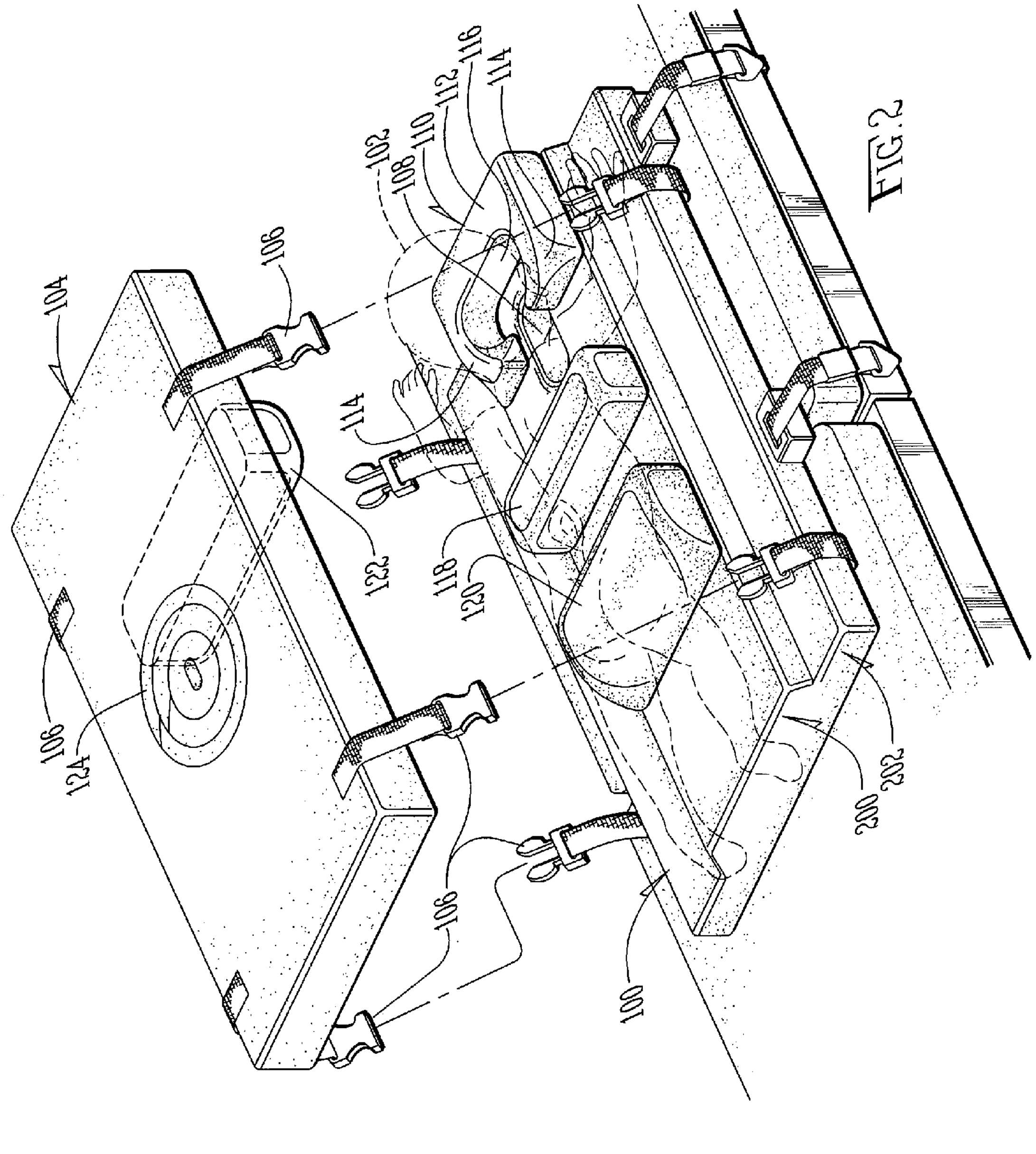
FIG. 2 is a perspective view of an embodiment of the positioning device.

Referring now to FIG. 2, a perspective view of an embodiment of the positioning device is depicted with a patient 102 depicted in dashed lines. In this view the patient has already been placed on the frontal support 100, which is disposed beneath the patient with the patient-facing surface oriented upwardly to receive the frontal surface of the patient. The posterior support is shown in an exploded configuration for clarity.

During typical use, the patient would first be disposed on the posterior support 104 in a supine position, after the dorsal opening 124 has been adjusted to the appropriate size for the patient. While in the supine position, and before the frontal support 100 has been installed, medical personnel may prepare the patient for the surgical procedure such as by administering anesthesia, placing IV's, lines and tubes as necessary in the arms, mouth and chest of the patient. The frontal support 100 is then positioned over the patient and the lines and tubes are arranged through the openings in the frontal support 100. Then the frontal support 100 is attached to the posterior support 104, securely retaining the patient between the two supports. Once secured, the patient can be rotated from the supine to the prone position and placed on the surgical table for the procedure. After the procedure, the patient may be rotated back onto the posterior support in a supine position, for post-operative care. The posterior support 104 provides support to the patient without pressure or damage to the area of the spinal exposure.

During surgery or other medical procedure, the patient is positioned in the prone position on the frontal support 100 with the head supported by facial support 110. Life support and monitoring connections are routed through the various apertures 108 in the frontal support 100 or along the sides of the frontal support 100. The patient's limbs are positioned over the support 100 to provide comfortable and non-damaging support to the patient during surgery, and the patient's pelvic and chest areas are supported by supports 118 and 120.

During surgery or other medical procedure, the posterior support 104 is positioned above the patient with its patient-facing surface oriented downward. In this position, the posterior support 104 may be positioned to provide neck and back support to the patient and to avoid unwanted contact with the exposed spinal material.

As described in relation to FIG. 1, the posterior support 104 comprises a base and one or more vertical supports, such as support 122, to provide ergonomic support to the patient 102 placed on the support 102. The support 104 may be sufficiently flexible to flex around the patient and contact the patient's body on a significant portion of the back of the head, neck, back and legs to provide secure support.

The posterior support 104 is also provided with an adjustable dorsal opening 124 to allow access to the affected area of the patient's back during surgery. The adjustable dorsal opening 124 may be provided in a variety of configurations, and, in embodiments, is adjustable to the patient. In the embodiment of the positioning device depicted in the figures, the adjustable dorsal opening 124 is provided by a spiral cut that begins in the center of the adjustable dorsal opening 124, and extends outwardly to the maximum extent of the adjustable dorsal opening 124.

In the depicted embodiment, the material in the adjustable dorsal opening 124 may be pulled upwardly out from the center of the spiral cut in a spiral strip. When sufficient material is pulled up from the posterior support 104 to provide the desired dorsal opening 124, then the spiral strip pulled from the center of the adjustable dorsal opening 124 is cut free and discarded, leaving an opening 124 to the patient's back.

When utilizing the positioning device with a patient, the posterior support 104 is disposed on a table or other secure area. The adjustable dorsal opening 124 is adjusted by the user to allow sufficient access to the myelomeningocele while still providing necessary support to the patient. As described above, the adjustment of the adjustable dorsal opening 124 may comprise pulling the spiral cut material up and away from the patient, and cutting off the extended material when the myelomeningocele is completely exposed. In other embodiments of the positioning device, the adjustable dorsal opening 124 may be provided in alternative means, such as pre-cut nested rings of material that may be removed from the opening 124 to adjust the size thereof.

The patient is placed on the posterior support 104 in the supine position and adjusted until all body parts and limbs are appropriately supported. After insertion of lines, anesthesia and other pre-operative procedures are complete, the frontal support 100 is positioned on the patient with adequate access to the mouth and nose is available through the headpiece for any required life support or diagnostic equipment, and secured to the posterior support 104.

Once the patient is properly positioned on the posterior support 104, the frontal support 100 is placed on top of the patient with the neck support 122 against the back of the patient's neck. After the frontal and posterior supports have been adjusted to the patient, the straps 106 are connected between the two supports 100 and 104 and tightened to exert sufficient pressure to retain the patient between the two supports 100 and 104 as positioned. At this time, the patient may be picked up and repositioned by manipulating the positioning device.

In various embodiments, the frontal support 100 may be formed with varying levels, such as raised central portion 200 or lowered edge portions 202.

In addition to allowing the patient to be placed in the prone and supine positions, the positioning device may also be placed on the sides of the supports 100 and 104 to position the patient in a lateral position.

Figure 3:
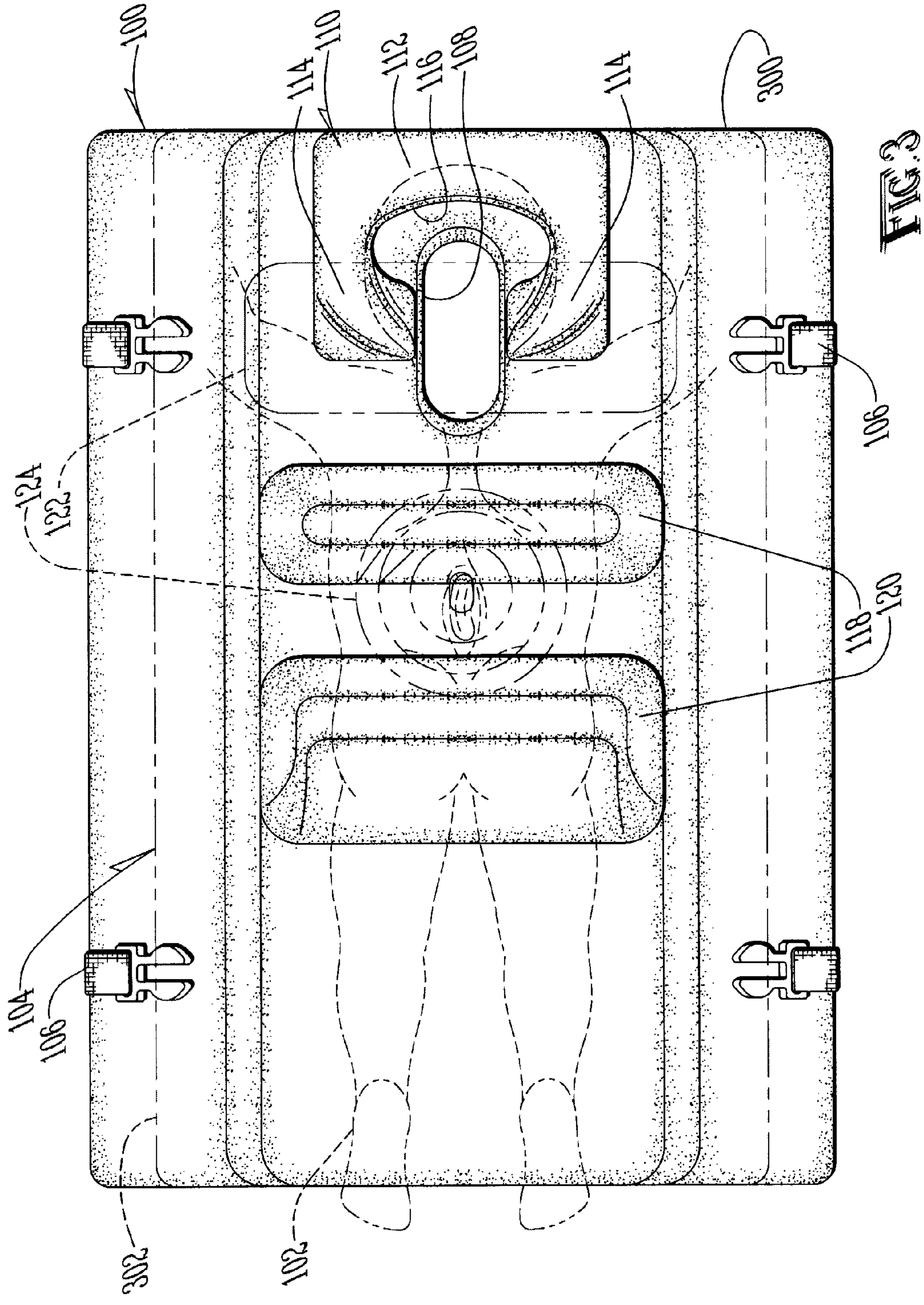
FIG. 3 is a top plan view of an embodiment of the positioning device.

Referring now to FIG. 3, a top plan view of an embodiment of the positioning device is depicted. The frontal support 100 is depicted in solid lines and the posterior support 106 is depicted in dashed lines. The frontal support 100 comprises a base 300 which provides a wide and stable platform on which the device rests during use. Extending upwardly from the base 300 are various supports that hold the various segments of the infant's body in the desired position.

In various embodiments of the positioning device, different supports may be provided than those shown in FIG. 3. The supports depicted in FIG. 3 include a facial support cushion 110 for supporting the head of the infant while allowing access to the face of the infant through the apertures 108 and 116 for the purpose of monitoring the breathing of the infant, for utilizing breathing tubes, and other similar life support, treatment and diagnostic purposes. Other supports, such as chest support cushion 118 and pelvic support cushion 120 are provided in various configurations to support the chest, limbs and body of the infant, while allowing needed access to the infant's body.

The posterior support 104 as depicted in FIG. 3 comprises a base 302 and neck support 122 attached thereto. In other embodiments of the device additional supports may be attached to posterior support 104.

Figure 4:
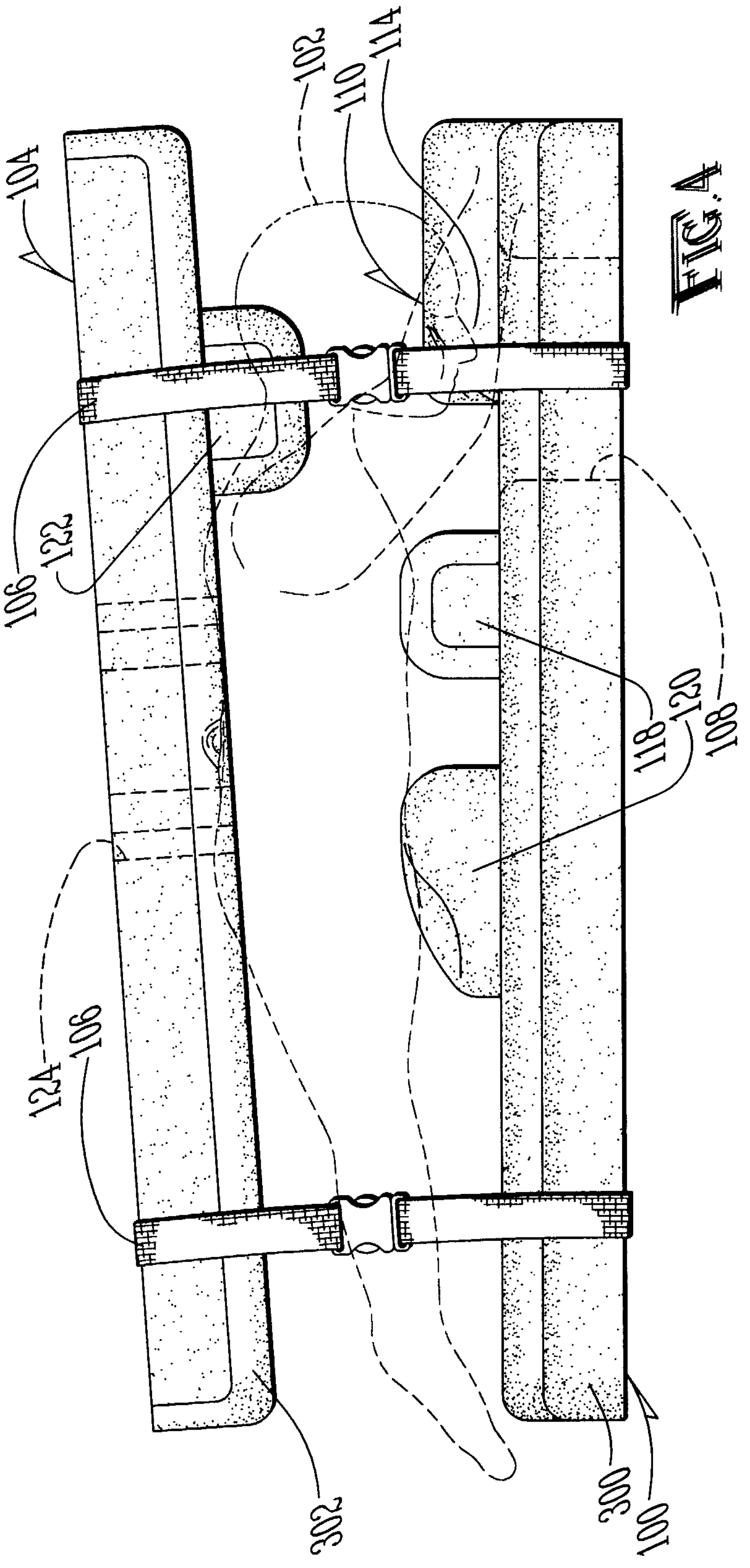
FIG. 4 is a side plan view of an embodiment of the positioning device.

Referring now to FIG. 4, a side plan view of an embodiment of the positioning device is depicted. The relationship between the patient 102, the frontal, or anterior, and posterior supports 100 and 104, and the various supports attached thereto, such as supports 110, 118, 120 and 122 provide numerous points of support through contact with the patient's body at the pelvis, chest, neck, forehead, and the back of the head. The affected area of the patient's back is accessible through adjustable dorsal opening 124.

Figure 5:
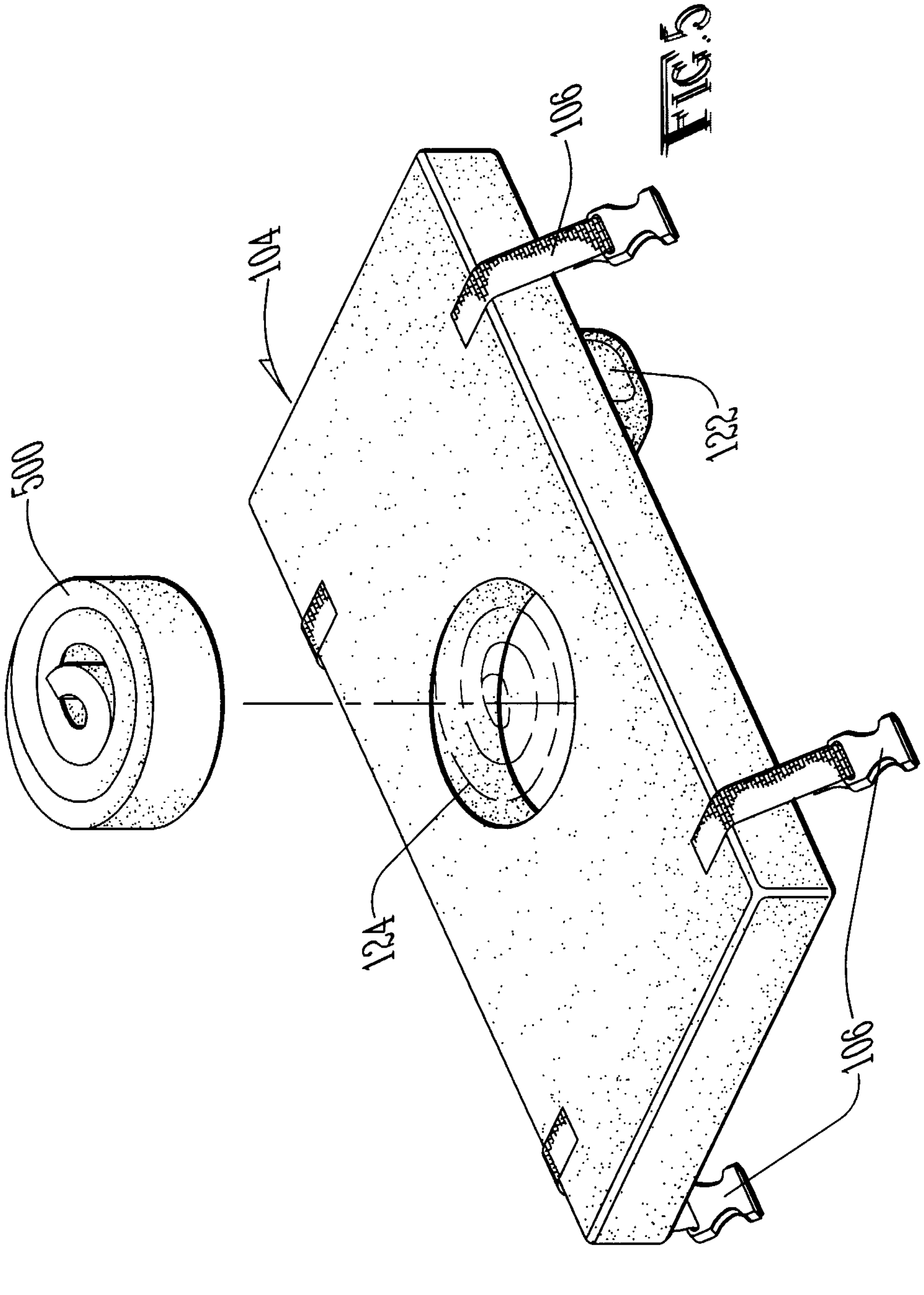
FIG. 5 is a perspective view of a portion of an embodiment of the positioning device.

Referring now to FIG. 5, a perspective view of a portion of an embodiment of the positioning device is depicted. As described above, the posterior support 104 is provided with an adjustable dorsal opening 124 for accessing the patient's back for treating the affected area. The adjustable dorsal opening 124 is initially filled with material 500 that is part of or similar to the base 302 of the posterior support 104, and may be unitary therewith. The area comprising the opening 124 is provided with cuts extending through base 302. In the embodiment shown in FIG. 5, the cut is in the shape of a spiral beginning at the center of opening 124. The user of the positioning device forms an opening 124 of the desired size by pulling the spiral cut material 500 from opening 124 beginning at the center. When a sufficient amount of material 500 has been removed from the opening 124 the user may cut the spiral strip across its width to remove the desired material from the opening 124.

Figure 6:
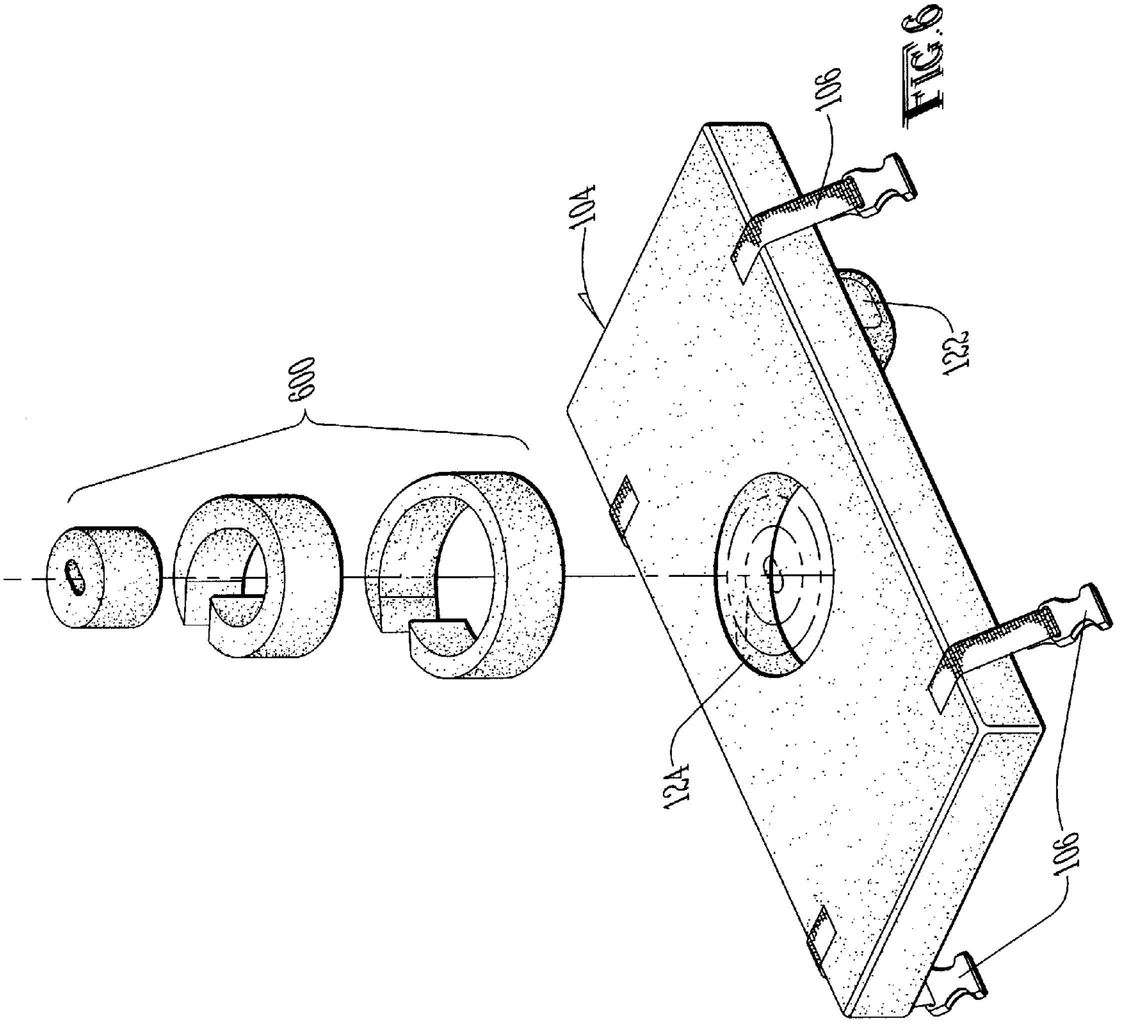
FIG. 6 is a perspective view of a portion of an alternative embodiment of the positioning device.

In other embodiments of the positioning device, the adjustable dorsal opening 124 may comprise pre-cut annular rings, nested squares, or other geometric configurations. One such alternative embodiment is depicted in FIG. 6, which utilizes annular rings 600 provided in the adjustable dorsal opening 124. The size of the adjustable dorsal opening 124 is varied in this embodiment by removing one or more of the annular rings 600 until the desired size is reached.

Figure 7:
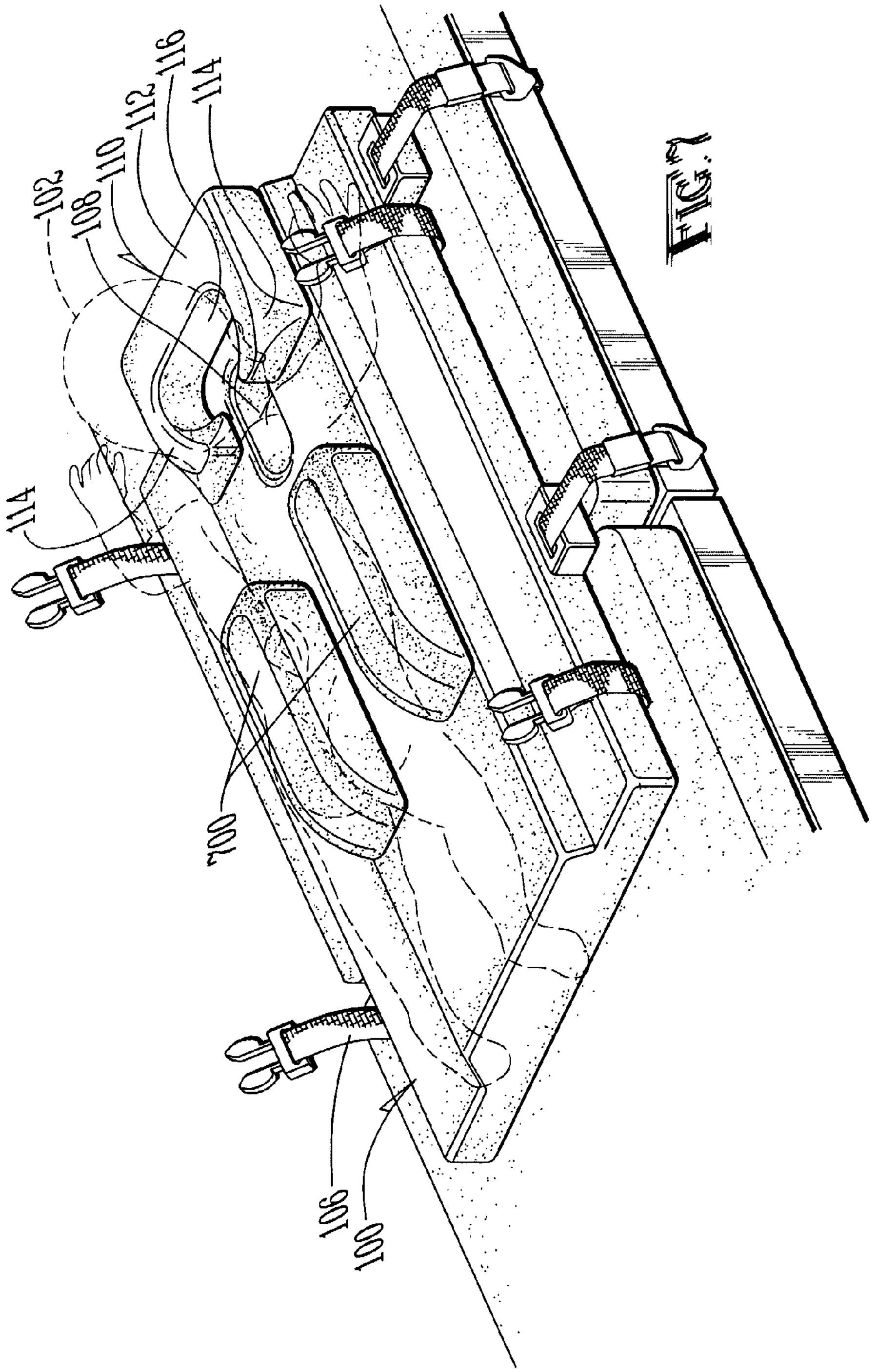
FIG. 7 is a perspective view of an alternative embodiment of the positioning device.

Referring now to FIG. 7, a perspective view of an alternate embodiment of the positioning device is depicted. In the alternative embodiment two longitudinal supports 700 are provided for supporting the patient's abdomen without impeding natural breathing.

Figure 8:
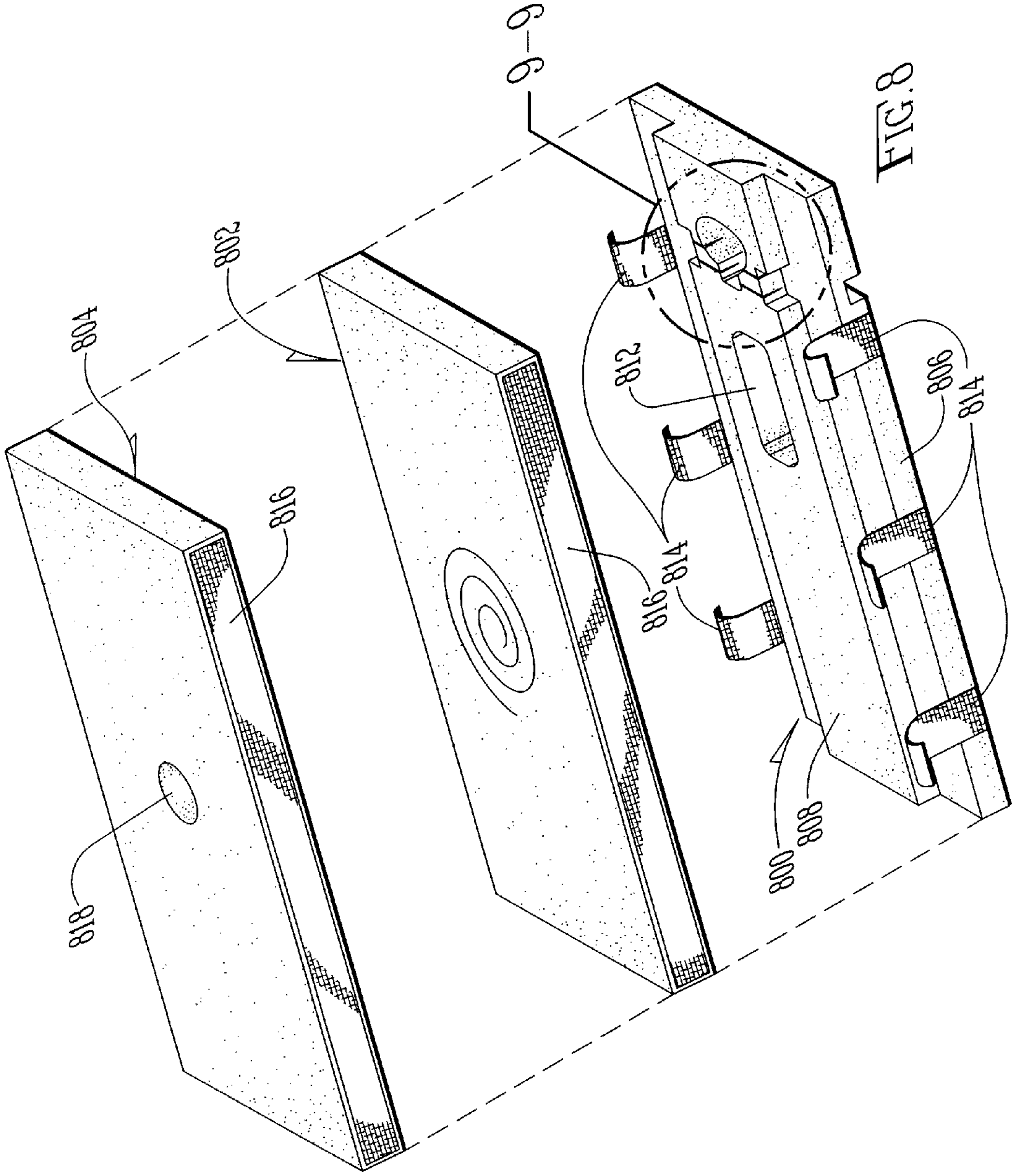
FIG. 8 is a perspective view of an alternative embodiment of the positioning device.

Referring now to FIG. 8, a perspective view of an alternate embodiment of the positioning device is depicted. In the alternative embodiment a third support pad for use after surgery is provided, and comprises frontal support 800, posterior surgery support 802 and posterior recovery support 804. In this embodiment, Frontal support 800 is provided with a base 806 and raised support 808 extending the length of the support 800. As in other embodiments, raised support 808 may be formed separately from or jointly with base 806. The support 800 is provided with a facial support area 810 identified as area 9-9 on FIG. 8 and described in more detail with respect to FIG. 9. Facial support area 810 comprises, in part, an aperture through support 800. The support 800 is also provided with an abdominal aperture 812 to ease breathing and to allow access to the patient for medical personnel. Support 800 is also provided with straps 814 attached thereto for securing the support 800 to supports 802 and 804 as desired. In the depicted embodiment the straps are provided with hook and loop closure material, but other methods and devices for fastening the straps may be used as provided as known in the art.

In the alternative embodiment, a posterior surgery support 802 is provided that is similar in form and function to the posterior support described in relation to earlier figures. The embodiment shown in FIG. 8 is provided with a fastening strip 816 of hoop and loop material for securing straps 814. Strip 816 may extend along the length of support 802 or may only extend for a portion, or separate portions, thereof. In the embodiment depicted in FIG. 8, posterior surgery support 802 is provided with no additional raised supports, such as support 122.

Posterior recovery support 804 is also provided for use during transport and after surgery is complete. The support 804 has a centrally located cut-out 818 that relieves pressure on the wound dressing, while providing better support to the lumbar and sacral area than the posterior surgery support 802. Support 804 is also provided with strip 816 or similar fastening means for securing the support 804 to support 800. In some embodiments, posterior recovery support 804 may be provided with straps to secure the patient to the support 804, optionally including a waist strap.

During typical use of the embodiment shown in FIG. 8, the same procedure for use of the positioning device with be utilized as that described above, however after the completion of the medical procedure, the posterior surgery support 802 is detached from the frontal support and removed from the patient while the patient is in the prone position. Then posterior recovery support 804 is disposed on the posterior of the patient with the dorsal opening 818 over the wound dressing area and secured to the frontal support 800. Then the patient may be transferred to a supine position for post-operative recovery and removal of the frontal support 800 when appropriate.

Figure 9:
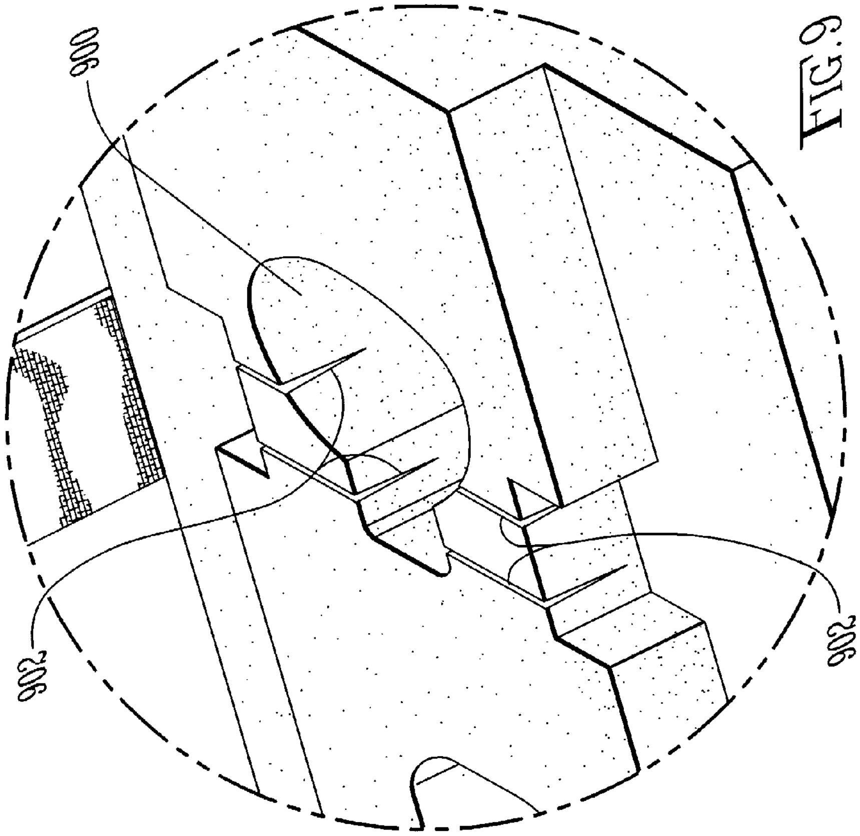
FIG. 9 is a detailed perspective view of an alternative embodiment of the positioning device.

Referring to FIG. 9, a detail perspective view of a portion of an embodiment of the positioning device is depicted. Specifically, the facial support area 810 of the embodiment shown in FIG. 8 and labeled as area 9-9 is depicted. The facial support area comprises an aperture 900 through support 800 to allow the patient to breathe, and to allow space for tubes, or various other instrumentation for diagnostic or life support of the patient to access the patient's mouth and nose. One or more slits 902 may be provided to accept and retain the tubes, wires or other items running to the patient's face. Slits 902 allow the tubes to be run over the top of the support 800 without contacting the patient's face and reducing the efficiency of the facial support area 810.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and combinations are of utility and may be employed without reference to other features and combinations and are contemplated within the scope of the claims. Not all steps listed in the various figures need be carried out in the specific order described.

What is claimed is:

1. A method of using a device for positioning a patient, the device comprising an anterior support, a surgical posterior support, and at least one strap for releasably connecting the anterior support to the posterior surgical support;

wherein the anterior support comprises a base formed from foam having a facial support area and a body support area on a top surface thereof; and wherein the surgical posterior support comprises a base with an adjustable dorsal opening therein extending from a top surface to a bottom surface thereof;

the method comprising the steps of:

adjusting the adjustable dorsal opening on the surgical posterior support as necessary for a patient;

placing a patient in a supine position on the surgical posterior support;

placing the anterior support on the anterior side of a patient with a patient's face located in the facial support area;

securing the anterior support to the surgical posterior support using the at least one strap;

rotating the device to the prone position; and operating on a patient through the adjustable dorsal opening.

2. The method of claim 1 wherein the adjustable dorsal opening comprises a spiral cut through the base of the surgical posterior support forming a spiral strip.

3. The method of claim 1, the device further comprising a post-surgery posterior support interchangeable with the surgical posterior support, said post-surgery posterior support comprising a base and a fixed dorsal opening therein, the method further comprising the steps of:

removing the surgical posterior support;

placing the post-surgery posterior support on the posterior side of a patient; and securing the post-surgery posterior support to the anterior support using the at least one strap.

* * * * *